US011138737B2

(12) United States Patent
Yokota et al.

(10) Patent No.: US 11,138,737 B2
(45) Date of Patent: Oct. 5, 2021

(54) METHOD AND APPARATUS FOR PREDICTING CELL REPROGRAMMING

(71) Applicants: Chung Yuan Christian University, Taoyuan (TW); RIKEN, Wako (JP)

(72) Inventors: Hideo Yokota, Wako (JP); Kuniya Abe, Tsukuba (JP); Ming-Dar Tsai, Taoyuan (TW); Slo-Li Chu, Taoyuan (TW); Yuan-Hsiang Chang, Taoyuan (TW)

(73) Assignees: CHUNG YUAN CHRISTIAN UNIVERSITY, Taoyuan (TW); RIKEN, Wako (JP)

( * ) Notice: Subject to any disclaimer, the term of this patent is extended or adjusted under 35 U.S.C. 154(b) by 7 days.

(21) Appl. No.: 16/719,905

(22) Filed: Dec. 18, 2019

(65) Prior Publication Data

US 2020/0126234 A1    Apr. 23, 2020

Related U.S. Application Data

(63) Continuation-in-part of application No. 15/894,945, filed on Feb. 13, 2018, now Pat. No. 10,586,327.

(51) Int. Cl.
| | |
|---|---|
| *G06K 9/00* | (2006.01) |
| *G06T 7/00* | (2017.01) |
| *G06T 7/11* | (2017.01) |
| *G06T 7/187* | (2017.01) |
| *G01N 33/50* | (2006.01) |
| *G02B 21/36* | (2006.01) |

(52) U.S. Cl.
CPC ....... *G06T 7/0016* (2013.01); *G01N 33/5005* (2013.01); *G06T 7/001* (2013.01); *G06T 7/11* (2017.01); *G06T 7/187* (2017.01); *G02B 21/367* (2013.01); *G06T 2207/10056* (2013.01); *G06T 2207/20076* (2013.01); *G06T 2207/20081* (2013.01); *G06T 2207/20084* (2013.01); *G06T 2207/20104* (2013.01); *G06T 2207/30024* (2013.01)

(58) Field of Classification Search
CPC .................................................. G06T 7/0016
See application file for complete search history.

(56) References Cited

U.S. PATENT DOCUMENTS

| | | | |
|---|---|---|---|
| 2017/0169567 A1* | 6/2017 | Chefd'hotel | G06T 7/0012 |
| 2020/0167914 A1* | 5/2020 | Stamatoyannopoulos | G06N 20/00 |
| 2020/0342597 A1* | 10/2020 | Chukka | G06T 7/194 |
| 2020/0380672 A1* | 12/2020 | Clark | G06N 20/10 |

\* cited by examiner

*Primary Examiner* — Oneal R Mistry

(57) ABSTRACT

Disclosed herein are methods for predicting the reprogramming process of cells from a microscopic image of one or more cells. According to some embodiments, the method includes capturing an image of region of interest (ROI) of every pixel of the microscopic image, followed by processing the ROI image with a trained convolutional neural network (CNN) model and a trained long short-term memory (LSTM) network so as to obtain predicted probability maps. Also disclosed herein are a storage medium and a system for executing the present methods.

7 Claims, 6 Drawing Sheets

| Class 1 | Class 2 | Class 2 | Class 3 | Class 3 |
|---|---|---|---|---|
|  |  |  |  |  |
|  |  |  |  |  |
|  |  |  |  |  |
|  |  |  |  |  |
|  |  |  |  |  |

METHOD AND APPARATUS FOR PREDICTING CELL REPROGRAMMING

CROSS REFERENCE TO RELATED APPLICATION

This application is a continuation-in-part of U.S. patent application Ser. No. 15/894,945, filed Feb. 13, 2018, which claims the benefit of Japanese Patent Application No. 2017-026477, filed on Feb. 15, 2017, the contents of said application are incorporated herein by reference in its entirety.

BACKGROUND OF THE INVENTION

1. Field of the Invention

The present disclosure in general relates to the prediction of cell reprogramming. More particularly, the present disclosure relates to methods and apparatuses for predicting the reprogramming status of cells at a time step in a temporal sequence from a microscopic image of one or more cells.

2. Description of Related Art

Induced pluripotent stem (iPS) cells are pluripotent cells generated from differentiated cells. In general, differentiated cells, such as fibroblasts, are induced into a pluripotent state by introducing genes encoding specific transcription factors into cells using viral vector, adenovirus, plasmid, and/or naked DNA. The thus-produced iPS cells may propagate indefinitely, and give rise to different cell types (e.g., neurons, heart cells, pancreatic cell, and liver cells) of a subject. It has been reported that iPS cells could be established from various mammalian cells, including human cells, and successfully induced into differentiated cells to make tissues or organ-like structures in vitro. Currently, clinical studies and trials, such as iPS cell-derived retinal pigment epithelium, have also been initiated. iPS cells represent an ideal source for patient-specific cell-based regenerative medicine and clinical studies.

However, the process for producing iPS cells is highly time-consuming and labor-intensive. It usually takes several months or even years for a skilled artisan to select and identify potential iPS cells from numerous candidate colonies. Further, the iPS induction efficiency is extremely low. For example, when using viral vectors, only a small subset of cells becomes the iPS cells within a vast population non-iPS cells, in which the efficiency for iPS cell induction ranges from 0.001-0.1%.

Recently, machining learning methods, such as convolution neural network (CNN), have been developed to detect colonies of iPS cells in microscopy images. Nonetheless, these methods merely identify the cells that have already reprogrammed into iPS cells, or the cells undergoing the reprogramming process. There is still a challenge to select and identify cells with reprogramming potential at an early stage. In view of the foregoing, there exists in the related art a need for a method capable of predicting the reprogramming status of cells, i.e., predicting the probability of cells reprogrammed from a differentiated state to a less differentiated state (e.g., being reprogrammed into iPS cells), so as to improve the speed and cost of the selection process.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method for predicting reprogramming status of cells at a time step in a temporal sequence from a microscopic image of one or more cells. According to embodiments of the present disclosure, the method comprises the steps of, (a) for every pixel of the microscopic image, capturing an image of a region of interest (ROI) of the pixel;

(b) applying a trained convolutional neural network (CNN) model to the captured ROI image to calculate the respective probabilities of the pixel belonging to any of a plurality of classes, wherein each of the plurality classes indicates a cell clustering pattern of the ROI image;

(c) processing the probabilities of the plurality of classes at the pixel by a trained long short-term memory (LSTM) network; and (d) producing a plurality of predicted probability maps respectively indicating the probabilities of the plurality of classes for every pixel of the microscopic image at the time step.

According to optional embodiments of the present disclosure, the method further comprises the steps of, (e) converting the microscopic image into a gray-level image according to the plurality of predicted probability maps; and (f) determining the reprogramming status of the gray-level image.

According to certain optional embodiments, the method further comprises the following steps to establish the trained CNN model:

(1) selecting a region of a CNN training image as a CNN template image;

(2) manually classifying the CNN template image to one of the plurality of classes;

(3) producing a CNN training set comprising a plurality of CNN template images from a plurality of CNN training images by repeating steps (1) and (2); and (4) using the plurality of CNN template images of the CNN training set as inputs to train a CNN architecture to produce the trained CNN model.

In optional embodiments, the plurality of CNN template images are divided into a first set of CNN template images and a second set of CNN template images, and the method further comprises the following steps to train the CNN model: using the first set of CNN template images to calculate a plurality of parameters of the CNN model; using the second set of CNN template images to calculate a plurality of error vectors of the plurality of parameters; and using the error vectors to re-calculate the parameters. For example, in some cases, a plurality of optimized parameters for the CNN model is produced after 10,000 iterations.

According to some optional embodiments, the method further comprises the following steps to establish the trained LSTM model:

(1) selecting a region of a LSTM training image as a LSTM template image;

(2) applying the trained CNN model to the LSTM template image to calculate the respective probabilities of the plurality of classes for every pixel of the LSTM template image;

(3) producing a LSTM training set comprising a plurality of LSTM template images from a plurality of LSTM training images by repeating steps (1) and (2); and (4) using the probabilities of the plurality of classes at each pixel of LSTM template images of the LSTM training set as inputs to train a LSTM architecture to produce the trained LSTM network.

In certain working examples of the present disclosure, the step (4) for establishing the trained LSTM network is performed by equations (1)-(6), $$f_t = \sigma(W_f \cdot [h_{t-1}, x_t] + b_f) \quad (1),$$

$$i_t = \sigma(W_i \cdot [h_{t-1}, x_t] + b_i) \quad (2),$$

$$c'_t = \tan h(W_c \cdot [h_{t-1}, x_t] + b_c) \quad (3),$$

$$c_t = f_t * c_{t-1} + i_t * c'_t \quad (4),$$

$$o_t = \sigma(W_o \cdot [h_{t-1}, x_t] + b_o) \quad (5),$$

$$h_t = o_t * \tan h(c_t) \quad (6),$$

where t is the time step in the temporal sequence, t−1 is a previous time step in the temporal sequence, σ is a sigmoid function, i is an input gate activation, f is a forget gate activation, o is an output gate activation, c is a cell activation, h is a cell output activation function, x is the probabilities of the plurality of classes at each pixel of the LSTM template image, each W is a weight matrix, and each b is a bias vector.

According to some embodiments of the present disclosure, the plurality of classes comprises a first, a second, and a third classes, wherein the first class indicates a first cell clustering pattern, in which no cell is present in the ROI image; the second class indicates a second cell clustering pattern, in which one or more differentiated cells are present in the ROI image; and the third class indicates a third cell clustering pattern, in which one or more reprograming or reprogrammed cells are present in the ROI image.

According to various embodiments of the present disclosure, the ROI image has a pixel size that is at least 113 by 113 pixels. Depending on intended purposes, the pixel sizes of the ROI image, the CNN template image, and the LSTM template image may be the same or different from one another.

In another aspect, the present disclosure is directed to a non-transitory, tangible computer-readable storage medium encoded with computer-readable instructions (a computer program or software) that when executed by a programmable device (a processor or a computer) cause the programmable device to perform the present methods for predicting the reprogramming status of cells from a microscopic image of one or more cells. All or various embodiments of the method according to the invention that are described herein can be executed by these encoded instructions when run in the programmable device.

In yet another aspect, the present invention is directed to a system for predicting the reprogramming status of cells at a time step in a temporal sequence from a microscopic image of one or more cells.

According to certain embodiments, the system comprises, an apparatus configured to obtain a microscopic image of one or more cells and a control unit that comprises a processor and a memory for storing a plurality of instructions which, when executed by the processor, causes the processor to perform the present method. All or various embodiments of the method according to the invention that are described herein can be executed by the processor.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

Figure 1:
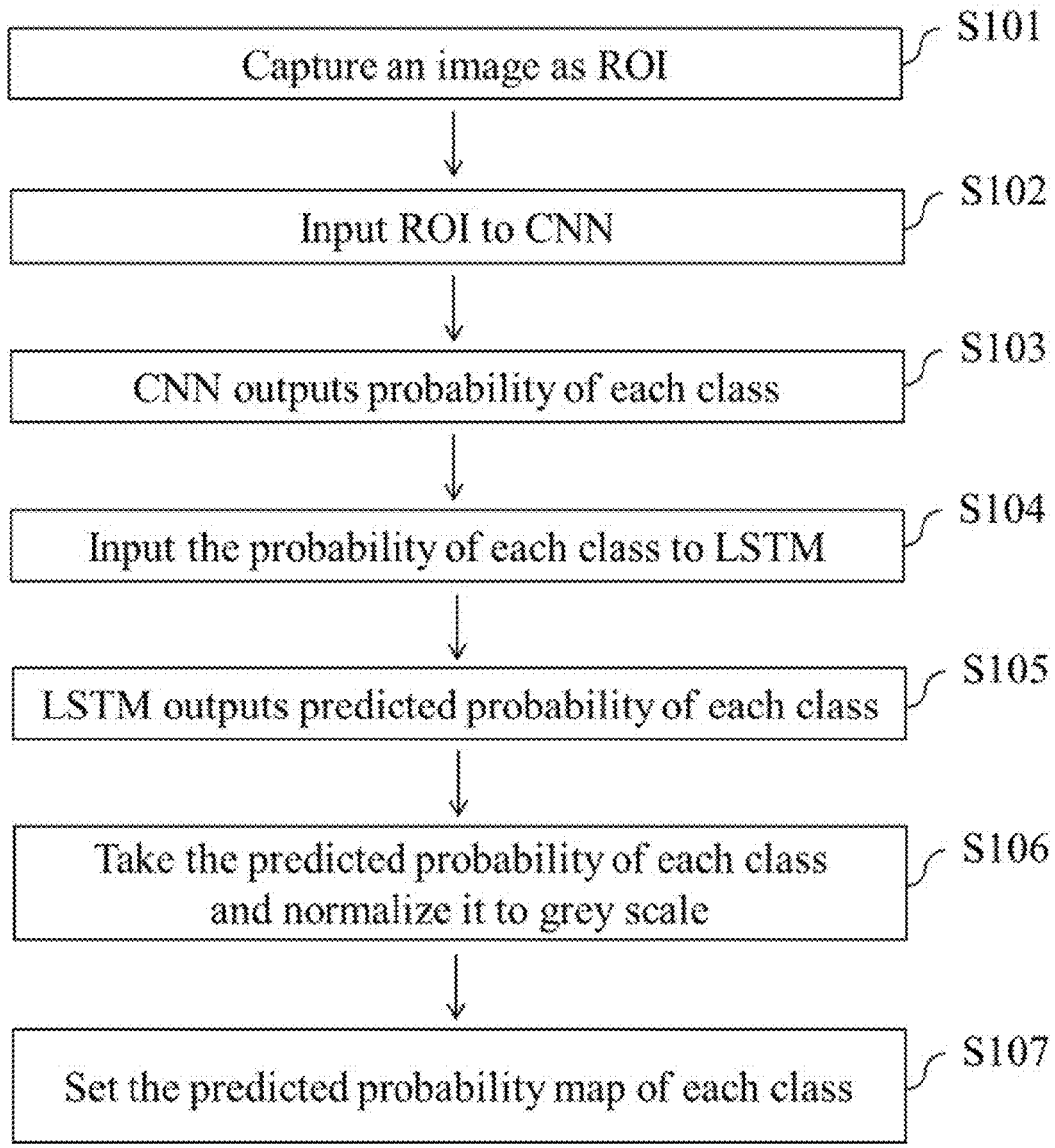
FIG. 1 is a flow diagram illustrating steps for performing a method 100 for predicting the reprogramming status of cells on an image according to the Embodiment 1 of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise.

Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "pluripotent" refers to a cell with the capacity, under different conditions, to differentiate to cell types characteristic of all three germ cell layers, i.e., endoderm (e.g., gut tissue), mesoderm (including blood, muscle, and vessels), and ectoderm (such as skin and nerve). Accordingly, the terms "pluripotency" or a "pluripotent state" as used herein refer to the developmental potential of a cell that provides the ability for the cell to differentiate into all three embryonic germ layers.

Throughout the present disclosure, the term, "induced pluripotent stem cells" or iPS cells, means that the stem cells are produced from differentiated adult cells that have been induced or changed (i.e., "reprogrammed") into cells capable of differentiating into tissues of all three germ or dermal layers.

The term "reprogramming" as used herein refers to the process of altering the differentiated state of a differentiated adult cell to a pluripotent phenotype. In other words, reprogramming refers to a process of driving a cell to a state with higher developmental potential, i.e., backwards to a less differentiated state. In some embodiments of the aspects described herein, reprogramming encompasses a complete or partial reversion of the differentiation state, i.e., an increase in the developmental potential of a cell, to that of a cell having a pluripotent state. Therefore, in some cases, the reprogramming of the present invention provides at least one dedifferentiated and/or rejuvenated cell, in particular provides a cell having the characteristic of a multi-potent, in particular pluripotent stem cell. The resulting cells are referred to herein as "reprogrammed cells."

As used herein, the term "differentiated cell" refers to a cell in the process of differentiating into a somatic cell lineage or having terminally differentiated. More specifically, the term "differentiated cell" refers to a cell having a specialized function and form (e.g., muscle cells, neurons, etc.). Unlike stem cells, differentiated cells have no or little pluripotency. Examples of differentiated cells include epidermal cells, epithelial cells, fibroblasts, pancreatic parenchymal cells, pancreatic duct cells, hepatic cells, blood cells, cardiac muscle cells, skeletal muscle cells, osteoblasts, skeletal myoblasts, neurons, endothelial cells, pigment cells, smooth muscle cells, adipocytes, bone cells, chondrocytes, and the like. According to some embodiments of the present disclosure, the differentiated cell is a cell differentiated from $CD34^+$ cell, and exhibits an adhesive morphology, i.e., being adhesive to a supporting substrate (e.g., a cell culture dish). In one specific example, the differentiated cell exhibits an epithelium-like morphology.

The term "predict" or "prediction" means to determine or tell in advance. When used to "predict" the reprogramming status of cells, for example, the term "predict" can mean that the likelihood of the outcome of the reprogramming status can be determined before the reprogramming process has progressed substantially.

The term "time step" as used herein refers to the difference in time from a determination of the conditions within a computational cell (e.g., the cell of the microscopic image) to a subsequent determination of the conditions within the computational cell.

II. Description of the Invention

Embodiment 1

The present disclosure aims at providing a method for predicting the reprogramming status of cells from a microscopic image of one or more cells.

FIG. 1 is a flow char illustrating steps of a method 100 for predicting the reprogramming status of cells via image analysis according to embodiments of the present disclosure. In the method 100, a microscopic image is taken, then for every pixel of the microscopic image, a plurality of images of a region of interest (ROI) are captured (S101). Specifically, in the step S101, every pixel of the microscopic image is processed by respectively assigning each pixel (x,y) to be the center of the ROI image. The ROI image of the present disclosure is not limited to certain pixel sizes; exemplary pixel size of the ROI image includes, but is not limited to, 32×32, 64×64, 113×113, 128×128, or 256×256 pixels. Preferably, the ROI image has a size of 113×113 pixels. As could be appreciated, a pixel size greater than 113×113 (e.g., 256×256) is also encompassed by the present disclosure According to some optional embodiments of the present disclosure, prior to the step S101, the method 100 further comprises the steps of partitioning the microscopic image into a plurality of chunks characterized by a chunk size, and then, the microscopic image is taken on a chunk by chunk basis. The chunk size of the microscopic image is not limited to certain sizes; exemplary chunk size of the microscopic image includes, but is not limited to, 11×1, 1×11, 11×11, and 53×1 (width×height) pixels. In one specific embodiment, compared to the microscopic images taken on a pixel by pixel basis, or the microscopic image taken by other chunk sizes, the microscopic image taken by a chunk size of 11×1 pixels may be used to predict the reprogramming status of cells in a more efficient and accurate manner.

Figure 2:
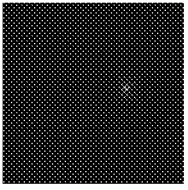
FIG. 2 depicts exemplary images for each of the classification in the Embodiment 1 of the present disclosure.
Figure 2:
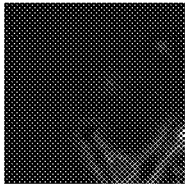
Figure 2:
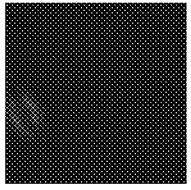
Figure 2:
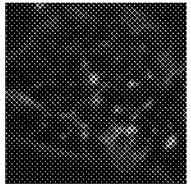
Figure 2:
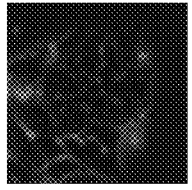
Figure 2:
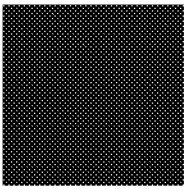
Figure 2:
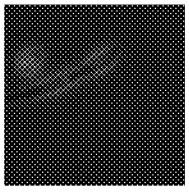
Figure 2:
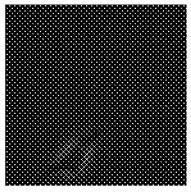
Figure 2:
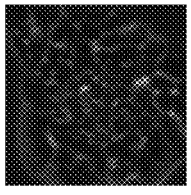
Figure 2:
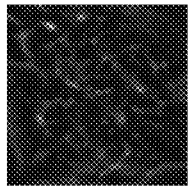
Figure 2:
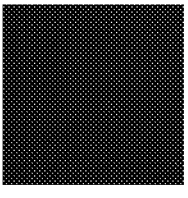
Figure 2:
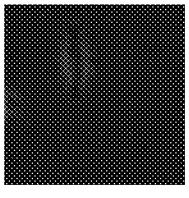
Figure 2:
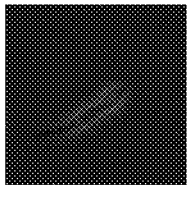
Figure 2:
Figure 2:
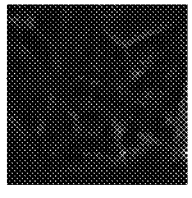
Figure 2:
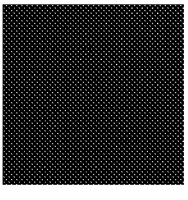
Figure 2:
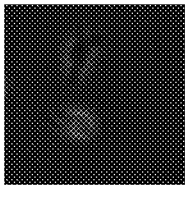
Figure 2:
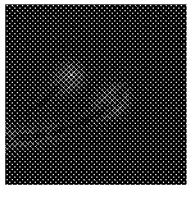
Figure 2:
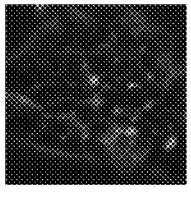
Figure 2:
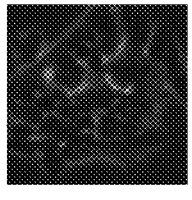
Figure 2:
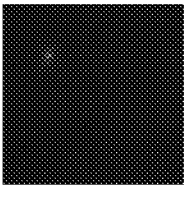
Figure 2:
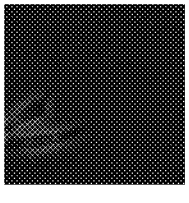
Figure 2:
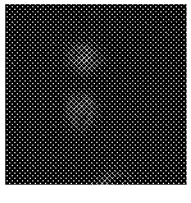
Figure 2:
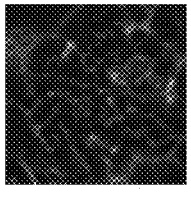
Figure 2:
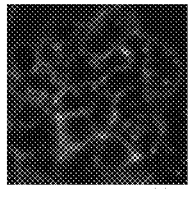

Then, the captured ROI image is used as an input of a trained convolutional neural network (CNN) model (S102), which calculates and outputs the probability of each pixel of the ROI image (S103), in which the probabilities of each and every pixels are assigned to a plurality of classes, with each class refers to a cell clustering pattern. According to some embodiments of the present disclosure, three cell clustering patterns are classified. For class 1, it refers to the class that no cell is present in the field of the ROI image. Regarding class 2, it refers to the class that one or more differentiated cells are present in the field of the ROI image. In class 3, it refers to the class that one or more reprograming or reprogrammed cells are present in the field of the ROI image. Reference is now made to FIG. 2, which are representative images for each of the 3 classes indicated above. According to some working examples, the differentiated cells in the class 2 may be any cell exhibiting an adhesive morphology; for example, epithelial cells, fibroblasts, muscles cells, or endothelial cells. In one specific example, the differentiated cells in the class 2 are derived from $CD34^+$ cells, and exhibit an epithelium-like morphology. As to the reprograming or reprogrammed cells in the class 3, they are preferably reprograming or reprogrammed iPS cells. According to certain working examples, the reprograming or reprogrammed cells in the class 3 appear to be rounded up and less adhesive to a supporting substrate (e.g., a cell culture dish) as compared to the differentiated cells in the class 2.

The calculated probability of each class for each pixel of the ROI image in S103 is then used as an input of a trained long short-term memory (LSTM) network (S104), which is a type of artificial recurrent neural network (RNN) architecture used in the field of deep learning, so as to produce the predicted probability of each class for each pixel of the ROI image at a time step in a temporal sequence (S105).

The method then proceeds to step S106, in which the predicted probability of each class in S105 is normalized to a grey scale in the range of 0-255.

Next, the predicted probability map of each class is generated (S107). In certain embodiments, the normalized grey scale values of three classes of each ROI are used to represent the predicted probability map of the corresponding (x, y) pixel at the center of the ROI. Accordingly, a skilled artisan may predict the reprogramming status of cells in the microscopic image at a specific time step in the temporal sequence via assigning the predicted probability map to the microscopic image.

Alternatively or optionally, the present method 100 may further comprise a step of gray-scale conversion, in which the original microscopic image is converted into a gray-level image using the predicted probability map data obtained in the step S107. Still optionally, the method may further comprise a determination step, in which the reprogramming status of cells in the microscopic image at a specific time step in the temporal sequence is determined based on the converted gray-level image, which indicates a predicted reprogramming status of the cells at the specific time step.

As could be appreciated, although in this embodiment, the normalization step S106 is performed before the step S107, however, in an alternative embodiment, the predicted probability map may also be generated directly from the predicted probability results, before being converted (or normalized) into grey scales. In such case, the step S107 in the method 100 precedes before the step S106. Still alternatively, the step S106 may be omitted; in such case, the predicted probability map is generated without any normalization step, and hence, the predicted probability map may be expressed as a fraction of one hundred (i.e., a value between 0% and 100%). In the case where no normalization step is performed, the predicted probability map may be converted into a gray-level image using other known techniques.

Also, it should be noted that according to certain embodiments of the present embodiments, not every predicted probability map of each class is normalized and/or converted into grey scale image(s). Rather, in some cases, only one or a selected number of classes is/are subjected to steps S106 and/or S107. For example, according to one embodiment, only the predicted probability map of class 2 is normalized and converted into a grey-scale image. In some alternative embodiments, only the predicted probability map of class 3 is normalized and converted into a grey-scale image.

According to some embodiments of the present disclosure, the method is used to predict the reprogramming status of $CD34^+$ cells from a microscopic image of the $CD34^+$ cells. In the optical field of a microscope, $CD34^+$ cells are non-adherent, and only cells undergoing reprogramming would adhere to a substrate (e.g., the culture dish), and accordingly, being captured on microscopic images.

The present method described above could be implemented using a non-transitory, tangible processor-readable storage medium having stored thereon processor-readable instructions that, when executed by the processor of a programmable device, control the programmable device to perform a method according to embodiments of the present disclosure. Exemplary processor-readable storage media suitable for implementing the subject matter described herein include, but are not limited to, random access memory (RAM), read-only memory (ROM), erasable programmable read-only memory (EPROM), electrically-erasable programmable read-only memory (EEPROM), flash memory, or other solid-state memory technologies, such as compact disc read-only memory (CD-ROM), digital versatile disc (DVD), or optical storage, magnetic cassettes, magnetic tape, magnetic disk storage or other magnetic storage devices, and any other medium, which can be used to store the desired information and which can be accessed by the processor. In addition, a processor-readable storage medium that implements the method described herein may be located on a single device or computing platform or may be distributed across multiple devices or computing platforms.

In another aspect of the present disclosure, a system for predicting the reprogramming status of cells at a time step in a temporal sequence from a microscopic image of one or more cells is provided. The system comprises an apparatus (hereinafter, an image-capturing apparatus) configured to obtain a microscopic image of one or more cells (e.g., $CD34^+$ cells), and a control unit. The image-capturing apparatus is, for example, any suitable optical microscope. The control unit is communicatively connected with the image-capturing apparatus, and is configured to process the microscopic images captured by the apparatus. In particular, the control unit comprises a processor, and a memory for storing a plurality of instructions, which, when executed by the processor, causes the processor to perform the present method(s).

The communication between the image-capturing apparatus and the control unit may be embodied using various techniques. For example, the system may comprise a network interface to permit communications between the image-capturing apparatus and the control unit over a network (such as a local area network (LAN), a wide area network (WAN), the internet, or a wireless network). In another example, the system may have a system bus that couples various system components, including the image-capturing apparatus and the control unit. In yet another embodiment, the system may have an output device for the image-capturing apparatus to output the data representing the microscopic image(s), and an input device for inputting these data into the control unit.

Figure 3:
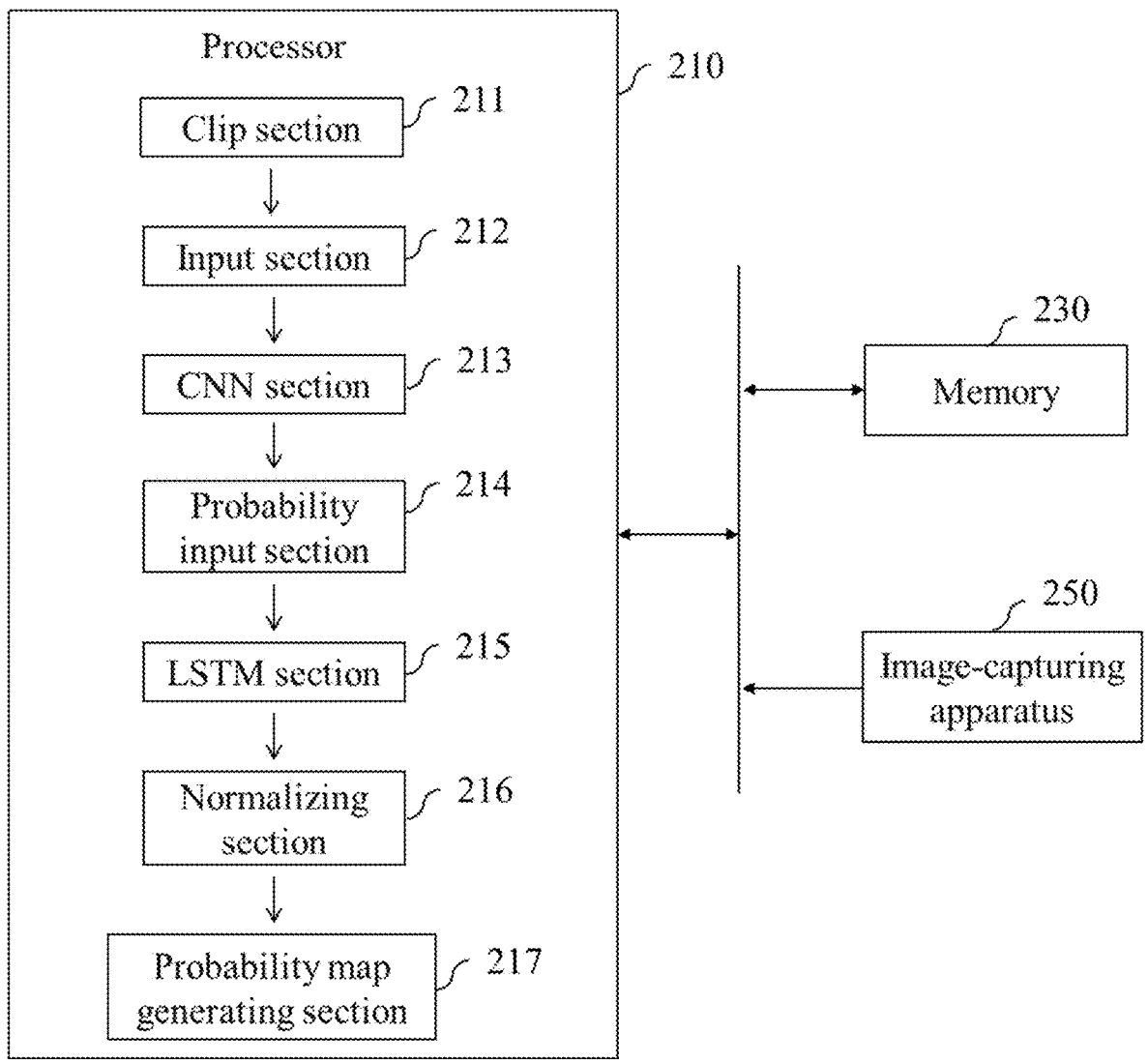
FIG. 3 is a block diagram of a system 200 for predicting the reprogramming status of cells on an image according to the Embodiment 1 of the present disclosure.

Reference is now made to FIG. 3, which is a block diagram of a system 200 for predicting the reprogramming status of cells at a time step in a temporal sequence from a microscopic image of one or more cells. The system 200 comprises a processor 210, a memory 230, and an image-capturing apparatus 250, in which the processor 210 comprises a clip section 211, an input section 212, a CNN section 213, a probability input section 214, a LSTM section 215, a normalizing section 216, and a probability map generating section 217. As depicted in FIG. 3, the processor 210, the memory 130, and the apparatus 250 are interconnected with one another via a system bus.

In operation, a microscopic image is first taken by the image-capturing apparatus 250 and used as an input image. Next, the input image is processed by the clip section 211 of the processor 210, which performs the step S101 of the method 100. The clip section 211 clips and captures the input image to produce a plurality of ROI images, which are then sent to the input section 212. The input section 212, which executes the step S102 of the method 100, inputs the ROI image(s) to the CNN section 213. The CNN section 213 carries out a calculation on the ROI images based on a CNN deep learning framework, and then outputs the probability of each pixel of the ROI image(s) expressed as a fraction of one hundred, in which the probability of each pixel belongs to one of a plurality of classes (i.e., the execution of the step S103 of the method 100). The probability of each class for each pixel of the ROI image(s) is then processed by the probability input section 214, which executes the step S104 of the method 100, and inputs the probability of each class for each pixel of the ROI image(s) to the LSTM section 215. The LSTM section 215 executes the step S105 of the method 100, which carries out a time series prediction with LSTM recurrent neural network, and then outputs the predicted probability of each class for each pixel of the ROI image(s) at different time steps in the time series to the normalizing section 216. The normalizing section 216 performs the step S106 of the method 100 so as to produce normalized value presenting the probability of each class for each pixel of the ROI image(s) in a grey scale. The normalized value is then processed by the probability map generating section 217, which performs the step S107 to produce the predicted probability map(s).

The memory 230 stores a plurality of instructions which, when executed by the processor 210, causes the processor to perform the steps S101-S107 of the present method 100 as explained above.

Optionally, the image 250 comprises a chunk section and a capture section. The chunk section is configured to partition the microscopic image into a plurality of chunks characterized by a chunk size (for example, 11×1 pixels). The partitioned microscopic image is then captured by the capture section, and used as in input image processed by clip section 211 of the processor 210.

Optionally, the system 200 further comprises a non-transitory, tangible computer-readable storage medium. Still optionally, the system 200 comprises one or more devices for accessing the instructions or codes stored in the non-transitory, tangible computer-readable storage medium, and storing said instructions or codes in the memory 230. Alternatively, the memory 230 is or comprises the non-transitory, tangible computer-readable storage medium that is encoded with the computer-readable instructions according to the present disclosure.

Embodiment 2

According to certain preferred embodiments of the present disclosure, the CNN section 213 as illustrated in FIG. 3 is a trained CNN architecture. For example, the CNN architecture may be trained using a conventional deep learning frame work with or without modifications. In the present case, the CNN architecture is trained using convolutional architecture for fast feature embedding (Caffe) with some modifications. Briefly, this architecture includes 8 layers, in which 5 layers are used for convolution, ReLU, and poolingm whereas 3 layers are fully connected. The instant modifications to the conventional Caffe architecture include: (1) image resolution is set as 113×113 pixels with no augmentation; (2) the processing order of pooling and the normalization is swapped; and (3) the results are 3 probabilities for the respective 3 classes (i.e., classes 1-3 of Embodiment 1).

Figure 4:
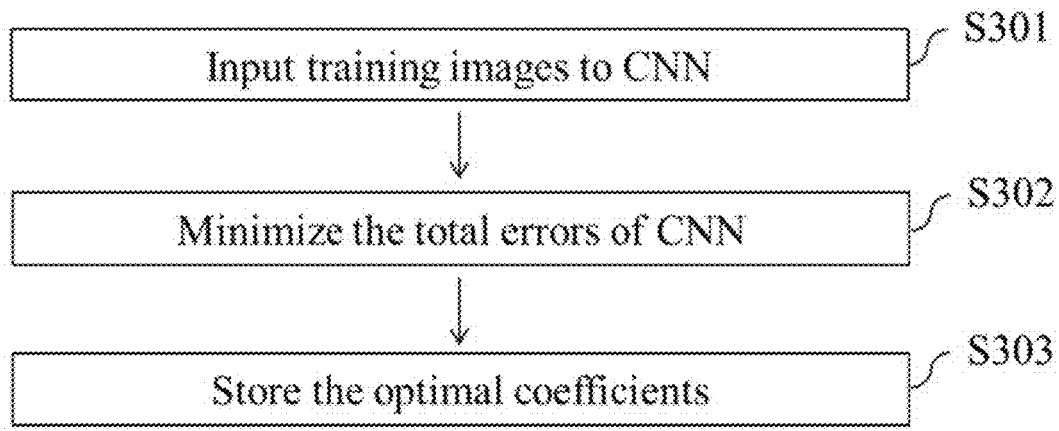
FIG. 4 is a flow diagram illustrating steps for performing a CNN training process 300 according to the Embodiment 2 of the present disclosure.

In this embodiment, the CNN training process 300 is implemented using the system 200 as illustrated in FIG. 3. Reference is now made to FIG. 4, which depicts a flow diagram illustrating steps S301, S302, S303 for training the CNN architecture of the CNN section 213.

First, one or more CNN training images are inputted to the clip section 211, which then clips and captures a plurality of CNN template images from each CNN training image, and delivers the CNN template images to the input section 212. The pixel size of the CNN template image may be the same or different from that of the ROI image described in Embodiment 1. For example, the pixel size of the CNN template image may be 32×32, 64×64, 113×113, 128×128, 256×256, or greater than 256×256 pixels. In preferred embodiments, the CNN template image has a pixel size of 113×113 pixels.

Then, the input section 212 feeds the CNN template images from the clip section 211 to the CNN section 213 (S301).

The CNN section 213 optimizes the parameters of the CNN architecture by iterating the plurality of CNN template images to minimize the total errors of the CNN deep learning framework (S302). Although the number of the CNN template images does not restrict the present embodiment, however, in one exemplary CNN training process, a total of 240 templates images (80 for each class) were extracted from 240 CNN training images. In this case, 60 CNN template images for each class are used for calculating the parameters of the CNN model, and 20 CNN template images for each class are used to calculate the error vectors of the parameters. The error vectors are then used to calculate the parameters again. The optimized parameters may be produced after 10,000 iterations.

The optimized parameters (that is, optimal coefficients) derived in the step S302 are stored in the memory 230 (S303).

As could be appreciated, the CNN section 213, together with the optimal coefficients, forms a trained CNN model that may be used for further analysis. For example, the system 200 with the trained CNN model may be used to perform the steps recited in FIG. 1. In this way, an image to be examined is fed to the system 200, in which the clip section 211 clips and capture the image to produce a plurality of ROI images, and the CNN section 213 outputs the probability (0%-100%) of each class for each pixel of the ROI images, i.e., classifying every pixel on the ROI images as 3 probabilities of the 3 classes. The probability of each class for every pixel on the ROI images is then provided to the LSTM section 215, which produces the predicted probability of each class of the pixels of the ROI images. Next, the probability map generating section 217 generates the predicted probability map based on the predicted probability. As an example, other than an imitation, the normalizing section 216 may take the probability of class 3 (iPS) and normalize it to grey scale (0-255); then, the probability map generating section 217 may generate the predicted probability map of class 3 by giving the grey scale value to its corresponding (x, y) pixel.

Embodiment 3

Figure 5:
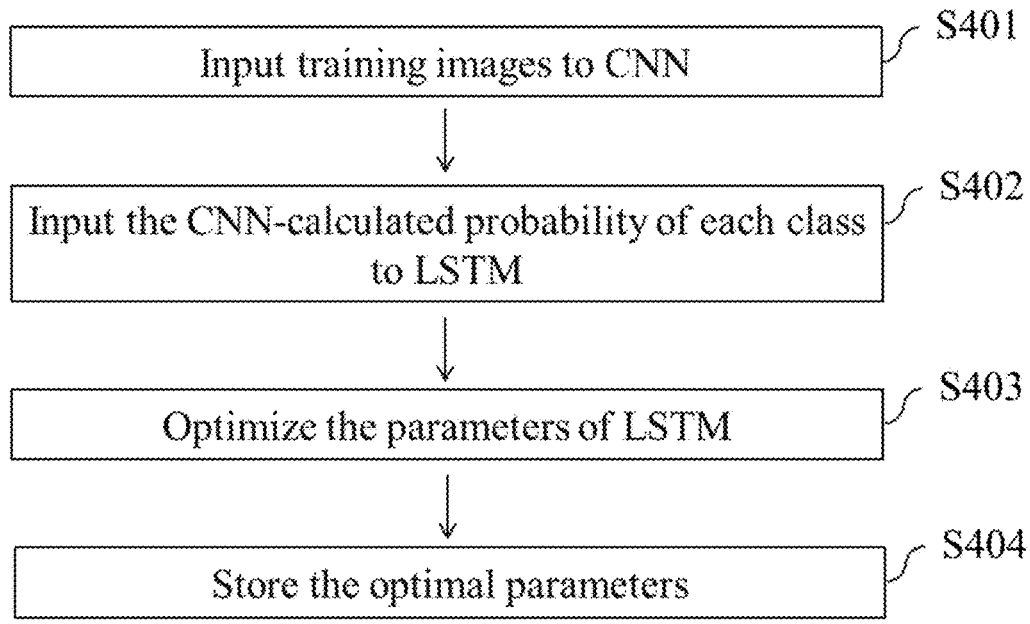
FIG. 5 is a flow diagram illustrating steps for performing a LSTM training process 400 according to the Embodiment 3 of the present disclosure.

According to some preferred embodiments of the present disclosure, the LSTM section 215 as illustrated in FIG. 3 is a trained LSTM network, which may predict the reprogramming status of cells by learning from a set of time-lapse microscopic images. In this embodiment, the LSTM training process 400 is implemented using the system 200 as illustrated in FIG. 3. Reference is made to FIG. 5, which is a flow diagram depicting the steps S401, S402, S403, S404 for training the LSTM network.

First, the microscopic images of cells in different differentiated states (e.g., from an undifferentiated state to a fully differentiated state) are used as LSTM training images, and inputted to the clip section 211, which clips and captures a plurality of LSTM template images from each LSTM training image, and then delivers the LSTM template images to the input section 212. As could be appreciated, the pixel size of the LSTM template image may be the same or different from that of the ROI image and the CNN template image as described in Embodiments 1 and 2 of the present disclosure, respectively. In some working examples, the LSTM template image has a pixel size (CNN bounding box) of 113× 113 pixels.

The input section 212 then feeds the LSTM template images from the clip section 211 to the CNN section 213 (S401), which, as mentioned above, calculates and outputs the probability of each class at every pixel of the LSTM template images to the probability input section 214.

The probability input section 214 then feeds the calculated probability of each class of the LSTM template images to the LSTM section 215 (S402).

Next, the LSTM section 215 optimizes the parameters of the LSTM architecture (S403) by iterating a plurality of the calculated probabilities of the 3 classes via equations (1)-(6):

$$f_t = \sigma(W_f \cdot [h_{t-1}, x_t] + b_f) \quad (1),$$

$$i_t = \sigma(W_i \cdot [h_{t-1}, x_t] + b_i) \quad (2),$$

$$c'_t = \tan h(W_c \cdot [h_{t-1}, x_t] + b_c) \quad (3),$$

$$c_t = f_t * c_{t-1} + i_t * c'_t \quad (4),$$

$$o_t = \sigma(W_o \cdot [h_{t-1}, x_t] + b_o) \quad (5),$$

$$h_t = o_t * \tan h(c_t) \quad (6),$$

where t is the time step in the temporal sequence, t−1 is a previous time step in the temporal sequence, σ is a sigmoid function, i is an input gate activation, f is a forget gate activation, o is an output gate activation, c is a cell activation, h is a cell output activation function, x is the probabilities of the plurality of classes at each pixel of the LSTM template image, each W is a weight matrix, and each b is a bias vector.

According to certain embodiments of the present disclosure, 160 time-lapse cell images with an interval of 20 minutes are used to train the LSTM network. In these embodiments, the chunk size of each LSTM template is 11×1, the batch size is 40, the time step for training is equal to or greater than (≥) 100, and the optimized parameters is obtained after 160 iterations.

The optimized parameters derived from the step S403 are stored in the memory 230 (S404).

As could be appreciated, the LSTM section 215, together with the optimal parameters, forms a trained LSTM network that may be used for further analysis. For example, the system 200 with the trained LSTM network may be used to perform the steps recited in FIG. 1. In this way, an image to be examined is fed to the system 200, in which the clip section 211 clips and capture the image to obtain a plurality of ROI images, and the CNN section 213 outputs the probability (0%-100%) of each class for each pixel of the ROI images, i.e., classifying every pixel on the ROI images as 3 probabilities of the 3 classes. The probability of each class for every pixel on the ROI images is then provided to the LSTM section 215, which produces the predicted probability of each class of the pixels of the ROI images. Next, the probability map generating section 217 generates the predicted probability map based on the predicted probability. As an example, other than an imitation, the normalizing section 216 may take the probability of class 3 (iPS) and normalize it to grey scale (0-255); then, the probability map generating section 217 may generate the predicted probability map of class 3 by giving the grey scale value to its corresponding (x, y) pixel. Next, the probability map generating section 217 generates the predicted probability map based on the predicted probability.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Generation of Human iPS Cells From Umbilical Cord Blood

Frozen human CD34$^+$ cells were thawed, washed with serum-free expansion medium (SFEM), and resuspended in expansion medium (SFEM supplemented with 20 ng/ml human stem cell factor (hSCF) and 50 ng/ml human thrombopoietin (hTPO)). Cells were then seeded into 24-well plates. After 24 hours of cultivation, the cells were collected, and episomal vectors carrying reprogramming factor genes were introduced into the cells by electroporation. After 72 hours of cultivation in the expansion medium, the cells were collected, washed, and resuspended in ES cell medium (DMEM/HAM-F12 supplemented with 20% knockout serum replacement, 1% non-essential amino acids, 2 mM L-glutamine, 0.1 mM 2-mercaproethanol, and 4 ng/ml human basic FGF) followed by seeding into matrigel-coated 6-well plates. Five days later, floating cells and ES medium were completely removed, and MTESR™ 1 was added to the culture. The culture medium was replaced every 2-3 days until human pluripotent stem cells-like cells appeared.

Image Database

Images of cell colonies undergoing iPS cell formation were taken using an incubator equipped with software, in which the mode of white balance was set to "auto"; meanwhile, exposure was set to "manual". The fluctuation of the exposure time was less than 10%, and the cells were almost uncolored. 107 sets of microscopic images have been obtained. Every set has effective 185 images with an interval of 20 minutes. All images were 12-bit images with a resolution of 1392×1040 pixels. These images were downsized into the resolution of 696×520. The original pixel width was about 0.65 μm.

Example 1 Establishing Training Models of the Present Method

Two training models were employed in the present example; they were CNN training model and LSTM training model. For the purpose of establishing the CNN training model, 240 CNN templates were manually classified to any of classes 1-3, including (1) class 1: region with no cells; (2) class 2: region with differentiated cells; and (3) class 3: region with possibly reprogramming and reprogrammed iPS cells. Each CNN template image had a size of 113×113 pixels. The CNN architecture was trained by these CNN template images using Caffe, which included 5 layers for Convolution, ReLU and Pooling, and 3 fully connected layers.

A LSTM network consisting of 100 of LSTM units was used to establish the LSTM training model. The input ($x_t$) was a 2D array with the probabilities of 3 classes (i.e., classes 1-3) for every pixel of LSTM template images, in which the sum of the 3 probabilities was 1. The output ($h_t$), cell state ($c_t$) and other values ($i_t$, $o_t$, f and $c'_t$) of each unit were also a 2D array with the probabilities of 3 classes for every pixel of the LSTM template images. Equations (1)-(6) were employed to optimize the parameters of LSTM units, including $W_f$, $W_i$, $W_c$, $W_o$, $b_f$, $b_i$, $b_c$ and $b_0$:

$$f_t = \sigma(W_f \cdot [h_{t-1}, x_t] + b_f) \quad (1),$$

$$i_t = \sigma(W_i \cdot [h_{t-1}, x_t] + b_i) \quad (2),$$

$$c'_t = \tan h(W_i \cdot [h_{t-1}, x_t] + b_c) \quad (3),$$

$$c_t = f_t * c_{t-1} + i_t * c'_t \quad (4),$$

$$o_t = \sigma(W_o \cdot [h_{t-1}, x_t] + b_o) \quad (5),$$

$$h_t = o_t * \tan h(c_t) \quad (6).$$

Each parameter of equations (1)-(6) were defined as in Embodiment 3 of the present disclosure, and the parameters of the LSTM units was optimized by a batch size of 40 after 160 iterations.

In the present example, LSTM training and prediction were implemented by multiple personal computers, equipped with Intel Core i7-8700, 64 GB Ram and graphics card of Asus dual-RTX2080. The software was developed using C/C++ programming and the OpenCV library. Meanwhile, the CNN training and classification were pre-processed and implemented in another computer.

Example 2 Prediction of Cellular Reprogramming Status by Use of the Present Method In this example, one microscopic image of CD34+ cells was processed by the training models established in Example 1, in which the pixels of the microscopic image was first classified by the CNN training model as 3 probabilities of the 3 classes, and then subjected to the process of softmax function of training LSTM model so as to produce the probability images reflecting the reprogramming status of the CD34+ cells at different time steps. In the LSTM units, the 2D dimensions of total pixels of the output images were the same size as the ones of the input images. A predicted output (as $h_{m+1}$) was then used as the input (as $x_{m+1}$) of the next LSTM unit in LSTM predictions, in which the trained LSTM parameters were used and not changed through the LSTM units for predictions.

Figure 6:
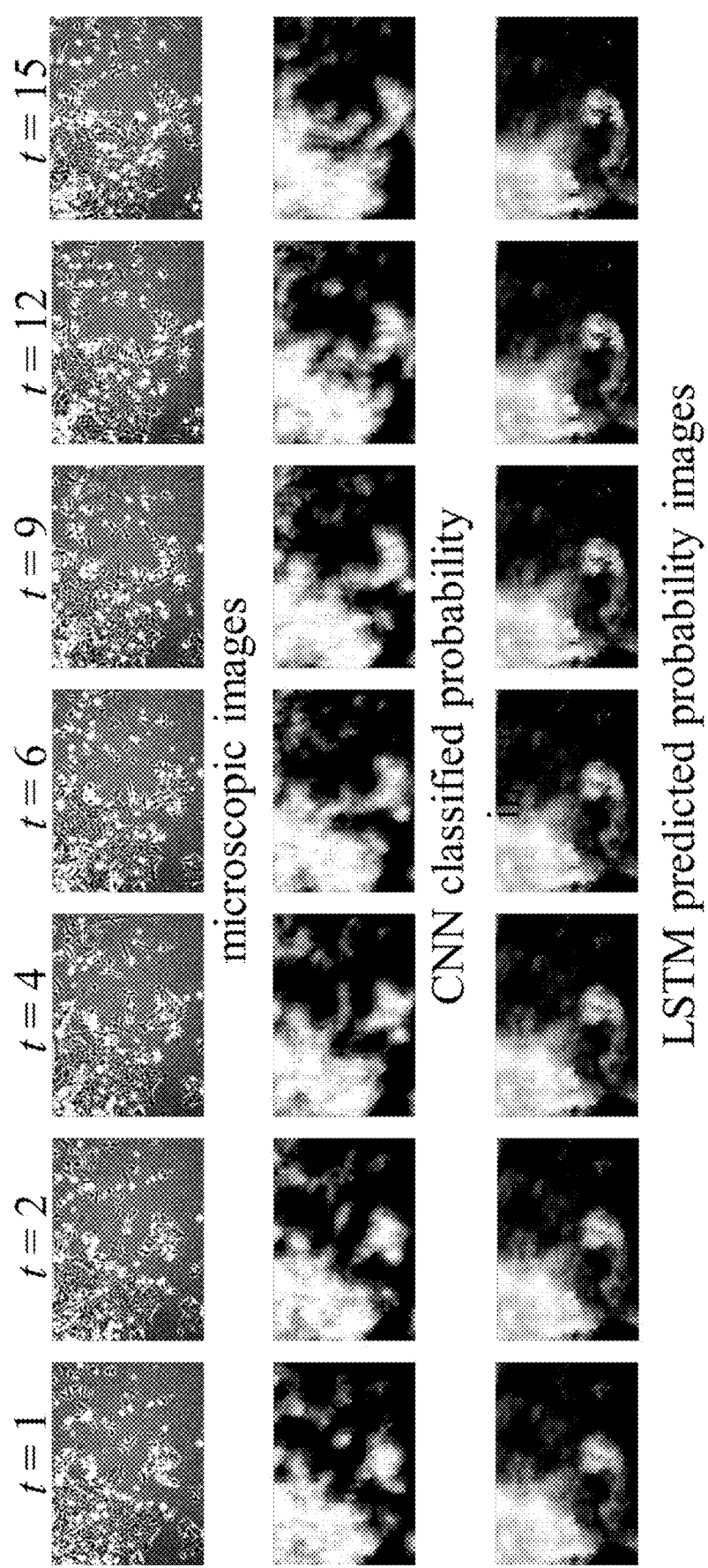
FIG. 6 depicts exemplary microscopic images, CNN classified probability images, and LSTM predicted probability images at specified time steps according to Example 2 of the present disclosure.
Figure 7:
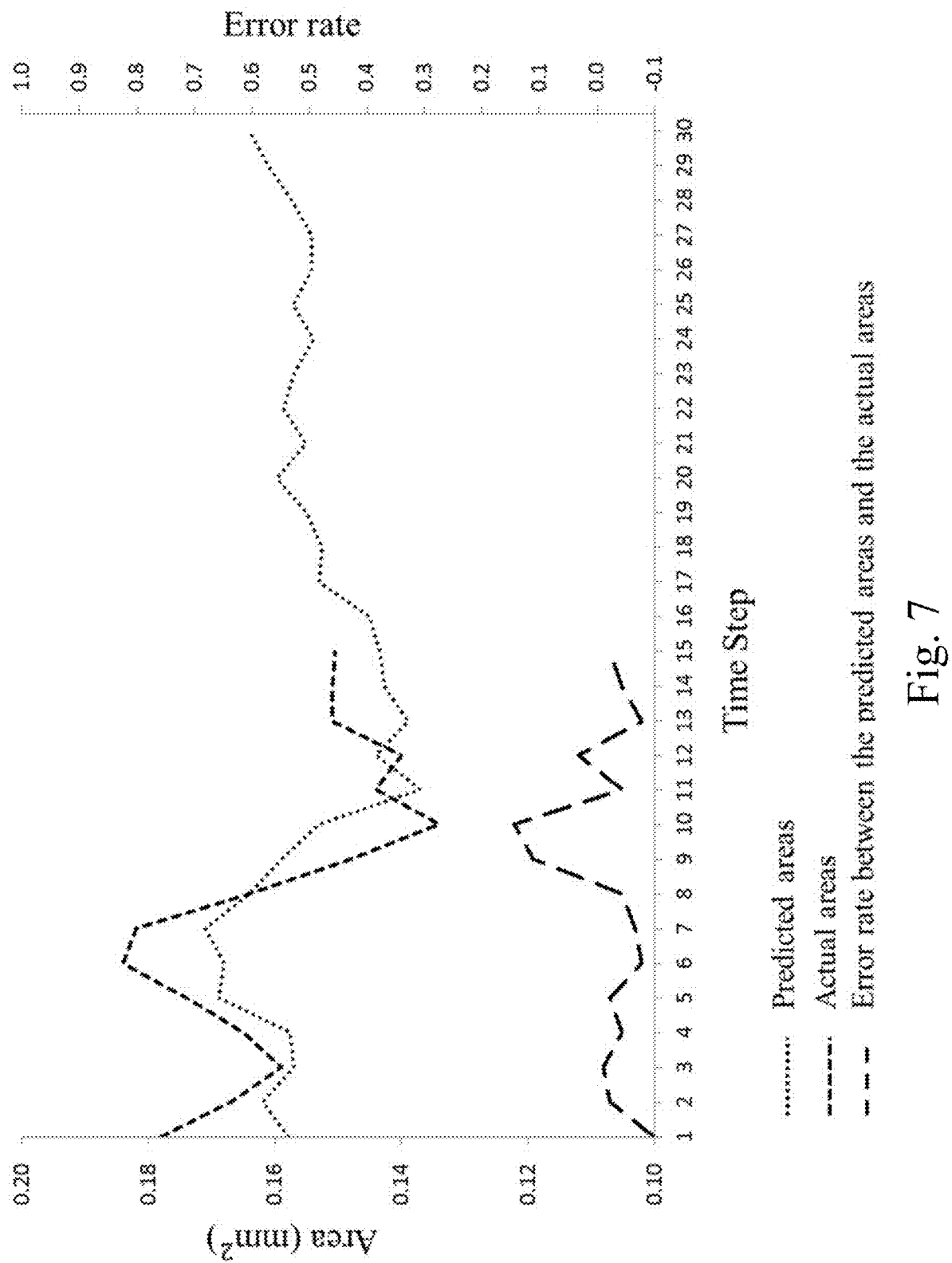
FIG. 7 depicts the areas of the CNN-classified iPS cell regions (actual areas) and the LSTM-predicted iPS cell regions (predicated areas) according to Example 2 of the present disclosure.

FIG. 6 depicted 6 probability images of CD34+ cells among 15 predicted time steps with the LSTM network trained by 160 sequent time-lapse cell images, as well as the CNN classified probability images from the actual cell images of some cell colonies in culturing. The probability values 0-1 corresponded the gray-levels 0-255 in the probability images. As the data of FIG. 6 indicated, the shapes of predicted and actual iPS cell regions were similar. FIG. 7 depicted the areas of the predicted iPS cell regions in 30 time steps, and the CNN classified iPS cells from the corresponding actual cell images. When the probability of class 3 of a pixel was greater than 50%, then such pixel would be considered as the iPS cell. The data of FIG. 7 demonstrated that the error rate between the predicted and actual areas was under 10%. Since the actual images were not yet generated in the 16-30 time steps, only the predicted results were shown in FIG. 7. The predicted area of iPS cell region grew stably after the 13$^{th}$ time step, although decreases temporarily in the 7-11 time steps (FIG. 7).

In conclusion, the present disclosure provides a method for predicting the reprogramming status of cells (for example, CD34+ cells) from a microscopic image of the cells. According to examples of the present disclosure, the shapes and cell areas of the cell images predicted by the present method matched that of the actual images at different time steps, in which the error rate was under 10%. Thus, a skilled artisan may efficiently select and identify cells (e.g., iPS cells) with reprogramming potential at an early stage, and focuses only on the promising colonies for molecular research and/or clinical application.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for predicting reprogramming status of cells at a time step in a temporal sequence from a microscopic image of one or more cells, comprising the steps of,
    (a) for every pixel of the microscopic image, capturing an image of a region of interest (ROI) of the pixel;
    (b) applying a trained convolutional neural network (CNN) model to the captured ROI image to calculate the respective probabilities of the pixel belonging to any of a plurality of classes, wherein each of the plurality classes indicates a cell clustering pattern of the captured ROI image;
    (c) processing the probabilities of the plurality of classes at the pixel by a trained long short-term memory (LSTM) network, wherein the trained LSTM network is established by a LSTM training method comprising the steps of,
        (1) selecting a region of a LSTM training image as a LSTM template image;

(2) applying the trained CNN model to the LSTM template image to calculate the respective probabilities of the plurality of classes for every pixel of the LSTM template image;
(3) producing a LSTM training set comprising a plurality of LSTM template images from a plurality of LSTM training images by repeating steps (1) and (2); and
(4) using the probabilities of the plurality of classes at each pixel of LSTM template images of the LSTM training set as inputs to train a LSTM architecture by equations (1)-(6) to produce the trained LSTM network, $$f_t = \sigma(W_f \cdot [h_{t-1}, x_t] + b_f) \quad (1),$$

$$i_t = \sigma(W_i \cdot [h_{t-1}, x_t] + b_i) \quad (2),$$

$$c'_t = \tan h(W_c \cdot [h_{t-1}, x_t] + b_c) \quad (3),$$

$$c_t = f_t * c_{t-1} + i_t * c'_t \quad (4),$$

$$o_t = \sigma(W_o \cdot [h_{t-1}, x_t] + b_o) \quad (5),$$

$$h_t = o_t * \tan h(c_t) \quad (6),$$

where t is the time step in the temporal sequence, t−1 is a previous time step in the temporal sequence, σ is a sigmoid function, i is an input gate activation, f is a forget gate activation, o is an output gate activation, c is a cell activation, h is a cell output activation function, x is the probabilities of the plurality of classes at each pixel of the LSTM template image, each W is a weight matrix, and each b is a bias vector; and
  (d) producing a plurality of predicted probability maps respectively indicating the probabilities of the plurality of classes for every pixel of the microscopic image at the time step.
2. The method of claim 1, further comprising the steps of,
(e) converting the microscopic image into a gray-level image according to the plurality of predicted probability maps; and
(f) determining the reprogramming status of the gray-level image.
3. The method of claim 1, wherein the captured ROI image has a pixel size that is at least 113 by 113 pixels.
4. The method of claim 1, wherein the trained CNN model is established by a CNN training method comprising the steps of,
  (1) selecting a region of a CNN training image as a CNN template image;
  (2) manually classifying the CNN template image to one of the plurality of classes;
  (3) producing a CNN training set comprising a plurality of CNN template images from a plurality of CNN training images by repeating steps (1) and (2); and
  (4) using the plurality of CNN template images of the CNN training set as inputs to train a CNN architecture to produce the trained CNN model.
5. The method of claim 4, wherein the plurality of CNN template images are divided into a first set of CNN template images and a second set of CNN template images, and in the step (4), the method comprises the steps of,
  using the first set of CNN template images to calculate a plurality of parameters of the CNN model;
  using the second set of CNN template images to calculate a plurality of error vectors of the plurality of parameters; and
  using the error vectors to re-calculate the parameters.
6. A non-transitory, tangible computer-readable storage medium, encoded with computer-readable instructions for executing the method of claim 1.
7. A system for predicting the reprogramming status of cells at a time step in a temporal sequence from a microscopic image of one or more cells, comprising,
  an apparatus configured to obtain a microscopic image of one or more cells; and
  a control unit, comprising a processor and a memory for storing a plurality of instructions which, when executed by the processor, causes the processor to perform the method of claim 1.

* * * * *